(12) United States Patent
Fang et al.

(10) Patent No.: US 12,383,198 B2
(45) Date of Patent: Aug. 12, 2025

(54) FINGER CLIP TYPE OXIMETRY DEVICE ADAPTIVE TO THICK AND THIN FINGERS

(71) Applicant: SHENZHEN NARIG BIO-MEDICAL TECHNOLOGY CO., LTD., Shenzhen (CN)

(72) Inventors: Jin Fang, Shenzhen (CN); Xiaocui Zhang, Shenzhen (CN)

(73) Assignee: Shenzhen Narig Bio-Medical Technology Co., Ltd., Shenzhen (CN)

(*) Notice: Subject to any disclaimer, the term of this patent is extended or adjusted under 35 U.S.C. 154(b) by 782 days.

(21) Appl. No.: 17/595,070

(22) PCT Filed: May 13, 2019

(86) PCT No.: PCT/CN2019/086619
§ 371 (c)(1),
(2) Date: Nov. 8, 2021

(87) PCT Pub. No.: WO2020/227887
PCT Pub. Date: Nov. 19, 2020

(65) Prior Publication Data
US 2022/0233143 A1    Jul. 28, 2022

(51) Int. Cl.
*A61B 5/00* (2006.01)
*A61B 5/0205* (2006.01)
(Continued)

(52) U.S. Cl.
CPC .......... *A61B 5/6826* (2013.01); *A61B 5/0205* (2013.01); *A61B 5/14552* (2013.01); *A61B 5/02427* (2013.01); *A61B 2560/0214* (2013.01)

(58) Field of Classification Search
CPC ............. A61B 5/02427; A61B 5/0205; A61B 5/14552; A61B 5/6826; A61B 2560/0214
See application file for complete search history.

(56) References Cited

U.S. PATENT DOCUMENTS

D718,455 S * 11/2014 Maser ................ D24/169
2001/0009265 A1* 7/2001 Schulz ............ A61B 5/02427
250/227.14
(Continued)

FOREIGN PATENT DOCUMENTS

CN    101411618 A    4/2009
CN    201585988 U    9/2010
(Continued)

OTHER PUBLICATIONS

CN 101411618 A English Translation (Year: 2009).*
CN 102648848 A English Translation (Year: 2012).*

*Primary Examiner* — Charles A Marmor, II
*Assistant Examiner* — Andrew E Hoffpauir
(74) *Attorney, Agent, or Firm* — Rosenberg, Klein & Lee (57) ABSTRACT

A finger clip type oximetry device adaptive to thick and thin fingers comprises a housing, an upper finger pad, a lower finger pad, a light emitting device and a receiver provided and a rotating mechanism. Wall surfaces of the upper and lower finger pads enclose an accommodating cavity. An opening is formed in one end of the accommodating cavity. An arc-shaped first contact surface is provided in an area of the lower finger pad in the accommodating cavity in contact with the pulp of the finger, and an arc-shaped second contact surface is provided in an area of the upper finger pad in the accommodating cavity in contact with the finger back. A first concave surface and second concave surfaces are provided along a transverse direction of the finger. The bending degree of the first concave surface is greater than that of the second concave surfaces.

15 Claims, 10 Drawing Sheets

(51) Int. Cl.
   *A61B 5/024*     (2006.01)
   *A61B 5/1455*    (2006.01)

(56) References Cited

U.S. PATENT DOCUMENTS

| | | | | |
|---|---|---|---|---|
| 2002/0156353 A1* | 10/2002 | Larson | ............... | A61B 5/14552 |
| | | | | 600/323 |
| 2003/0045784 A1* | 3/2003 | Palatnik | ............... | A61B 5/6826 |
| | | | | 600/323 |
| 2006/0106294 A1* | 5/2006 | Maser | ................ | A61B 5/6838 |
| | | | | 600/344 |
| 2006/0155198 A1* | 7/2006 | Schmid | ................ | A61B 5/6838 |
| | | | | 600/481 |
| 2008/0197301 A1* | 8/2008 | Diab | .................... | A61B 5/6826 |
| | | | | 250/505.1 |
| 2010/0004519 A1* | 1/2010 | Lamego | ............. | A61B 5/02427 |
| | | | | 250/216 |
| 2010/0305417 A1* | 12/2010 | Kumazaki | ............ | A61B 5/6838 |
| | | | | 600/323 |
| 2012/0016219 A1* | 1/2012 | Fujii | .................... | A61B 5/6826 |
| | | | | 600/324 |
| 2015/0045638 A1* | 2/2015 | Liu | ...................... | A61B 5/0205 |
| | | | | 600/324 |

FOREIGN PATENT DOCUMENTS

| | | | | | |
|---|---|---|---|---|---|
| CN | 102648848 A | * | 8/2012 | ......... | A61B 5/14552 |
| JP | S63-192422 A | | 8/1988 | | |

* cited by examiner

FINGER CLIP TYPE OXIMETRY DEVICE ADAPTIVE TO THICK AND THIN FINGERS

CROSS-REFERENCE TO RELATED APPLICATIONS

This application is the 371 of International Application No. PCT/CN2019/086619, filed May 13, 2019, the entire contents of which are incorporated herein by reference.

TECHNICAL FIELD

The present application relates to medical detection devices, and more particularly to a finger clip type oximetry device adaptive to thick and thin fingers.

BACKGROUND

A probe of a traditional finger clip type oximetry is mainly composed of an upper shell and a lower shell, a connecting spring, an upper finger pad, a lower finger pad and an optical sensor element. The upper finger pad is arranged on the upper shell, and the lower finger pad is arranged on the lower shell. The upper finger pad and the lower finger pad, for contacting human fingers, are made of flexible materials, thereby improving comfort while the finger contacts.

In traditional technology, the finger contact areas where the upper pad contacts the finger and where the lower finger pad contacts the finger are mainly made into an arc surface for contacting with the arc surface of the finger. However, it cannot be adaptive to fingers of different thickness and size since the upper finger pad and the lower finger pad each have only one arc surface, which is easy to cause interference of light leakage and affect the measurement result. If the finger pad has an arc surface with a larger curvature, the arc surface of the finger pad can fit well with the edges of the thick finger to meet the light shielding requirement while measuring a thick finger, but the finger pad cannot fit well with the edges of the thin finger while measuring a thin finger, since the arc surface of the finger pad is large, which will cause light leakage from the edges of the thin finger and affect the result. Alternatively, if the finger pad uniformly has an arc surface with a smaller curvature, the arc surface of the finger pad can fit well with the edges of the thin finger to meet the light shielding requirement while measuring a thin finger, but the thick finger cannot be put in or the edges of the thick finger are mainly exposed on the outside of the arc surface of the finger pad while measuring a thick finger, since the arc surface of the finger pad is small. Therefore, the thick finger cannot be wrapped well and the light leakage is caused, which will also affect the measurement result.

Therefore, the traditional technology has yet to be developed.

SUMMARY

There is provided a finger clip type oximetry device adaptive to thick and thin fingers according to embodiments of the present disclosure. The technical solution is as below:

According to a first aspect of embodiments of the present disclosure, there is provided a finger clip type oximetry device adaptive to thick and thin fingers, comprising:
 a finger clip type oximetry device adaptive to thick and thin fingers, comprising:
 a shell;
 an upper finger pad, a lower finger pad, a light emitter, and a receiver provided in the sell, wherein an accommodating cavity is enclosed by a wall surface of the upper finger pad and a wall surface of the lower finger pad for placing a finger to be measured; and
 a rotating mechanism for relatively opening or clamping the upper finger pad and the lower finger pad;
 wherein one end of the accommodating cavity is provided with an opening, wherein an arc-shaped first contact surface is provided at a contact area where the lower finger pad contacts a pulp of the finger in the accommodating cavity; and an arc-shaped second contact surface is provided at a contact area where the upper finger pad contacts a dorsal of the finger in the accommodating cavity, and
 wherein a first concave surface is arranged on a middle area of the arc-shaped first contact surface along a transverse direction of the finger, each of both sides of the first concave surface of the first contact surface is formed with a second concave surface, and a curvature of the first concave surface is greater than a curvature of the second concave surface.

BRIEF DESCRIPTION OF THE DRAWINGS

In order to explain the embodiments of the present disclosure or the technical solutions in the prior art more clearly, the following will briefly introduce the drawings that need to be used in the description of the embodiments or the prior art. Obviously, the drawings in the following description are only some embodiments of the present disclosure. For those of ordinary skill in the art, without creative work, other drawings can be obtained based on the structure shown in these drawings.

DESCRIPTION OF REFERENCE SIGNS

1—oximetry device, 10—shell, 11—upper shell, 111—upper cover, 112—upper bracket, 113—first outer shell, 12—lower shell, 121—lower cover, 122—lower bracket, 123—second outer shell, 21—upper finger pad, 22—lower finger pad, 211—end part, 31—light emitter, 32—receiver, 40—rotating mechanism, 41—mounting post, 42—spring, 421—middle part, 422—first end, 423—second end, 50—accommodating cavity, 51—opening, 61—first contact surface, 611—first concave surface, 6111—first mounting port, 612—second concave surface, 613—first arc surface, 614—second arc surface, 62—second contact surface, 621—second mounting port, 622—third concave surface, 623—fourth concave surface, 63—first light-shielding surface, 64—second light-shielding surface, 65—third light-shielding surface, 70—transparent contact layer, 81—first cavity, 82—second cavity, 91—control circuit board, 92—switch, and 93—battery.

DETAILED DESCRIPTION

The technical solutions in the embodiments of the present disclosure will be clearly and completely described below in conjunction with the accompanying drawings in the embodiments of the present disclosure. Obviously, the described embodiments are only a part of the embodiments of the present disclosure, rather than all the embodiments. Based on the embodiments of the present disclosure, all other embodiments obtained by those of ordinary skill in the art without creative work shall fall within the protection scope of the present disclosure.

Referring to FIGS. 1 to 4, a finger clip type oximetry device 1 is suitable for thick and thin fingers of the present disclosure, including a shell 10, an upper finger pad 21, a lower finger pad 22, a light emitter 31, and a receiver 32 arranged in the shell 10, and a rotating mechanism 40 for relatively opening or clamping the upper finger pad 21 and the lower finger pad 22. A wall surface of the upper finger pad 21 and a wall surface of the lower finger pad 22 enclose an accommodating cavity 50 for placing the finger to be measured. An opening 51 is provided at one end of the accommodating cavity 50. The upper finger pad 21 and the lower finger pad 22 in the embodiment of the present disclosure are made of flexible materials, and their mounting positions in the shell 10 are interchangeable. The light emitted by the light emitter 31 for oximetry passes through the finger and is received by the receiver 32. The shell 10 may be an integral structure or a structure with an upper shell and a lower shell. The rotating mechanism 40 may be an elastic clamping mechanism or a clamping mechanism capable of opening or clamping. The opening 51 of the accommodating cavity 50 in the embodiment of the present disclosure is used to allow the finger to be measured to be putted into the accommodating cavity 50. The light emitter 31 and the receiver 32 of the finger clip type oximetry device 1 of the present disclosure are connected to an external measurement system through a cable, so that the finger clip type oximetry device 1 of the present disclosure becomes an oximetry probe. Alternatively, the finger clip type oximetry device 1 of the present disclosure is provided with a measuring main board in the shell, and the light emitter 31 and the receiver 32 are directly connected to the measuring main board in the shell 10, so that the finger clip type oximetry device 1 of the present disclosure becomes a single oximetry instrument.

Figure 5:
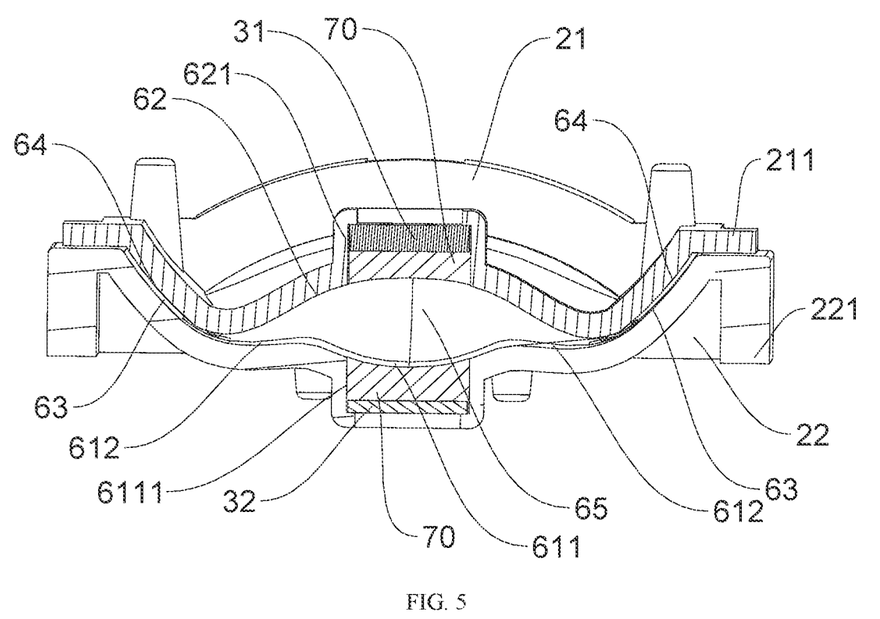
FIG. 5 is a schematic sectional view of an upper finger pad, a lower finger pad, a light emitter, and a receiver.
Figure 6:
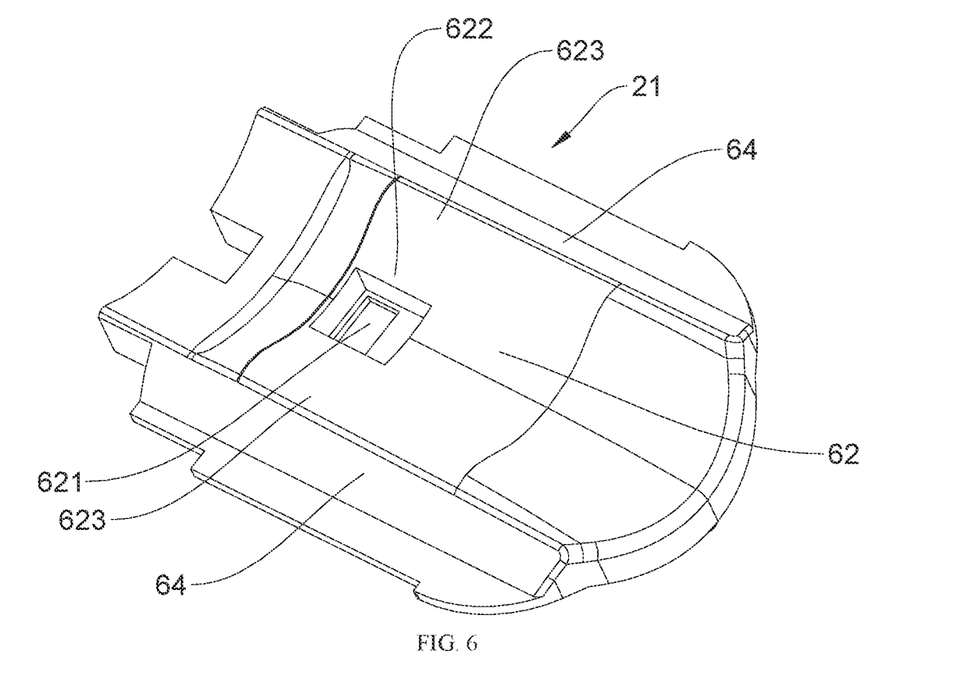
FIG. 6 is a schematic diagram of the structure of the upper finger pad in FIG. 2.

Referring to FIGS. 5 and 6, an arc-shaped first contact surface 61 is provided at the contact area where the lower finger pad 22 contacts the pulp of the finger in the accommodating cavity 50, and an arc-shaped second contact surface 62 is provided at the contact area where the upper finger pad 21 contacts the dorsal of the finger in the accommodating cavity 50. In the embodiment of the present disclosure, when the finger is placed in the accommodating cavity 50, the arc-shaped first contact surface 61 of the lower finger pad 22 contacts the pulp of the finger, and the arc-shaped second contact surface 62 of the upper finger pad 21 contacts the dorsal of the finger.

Figure 7:
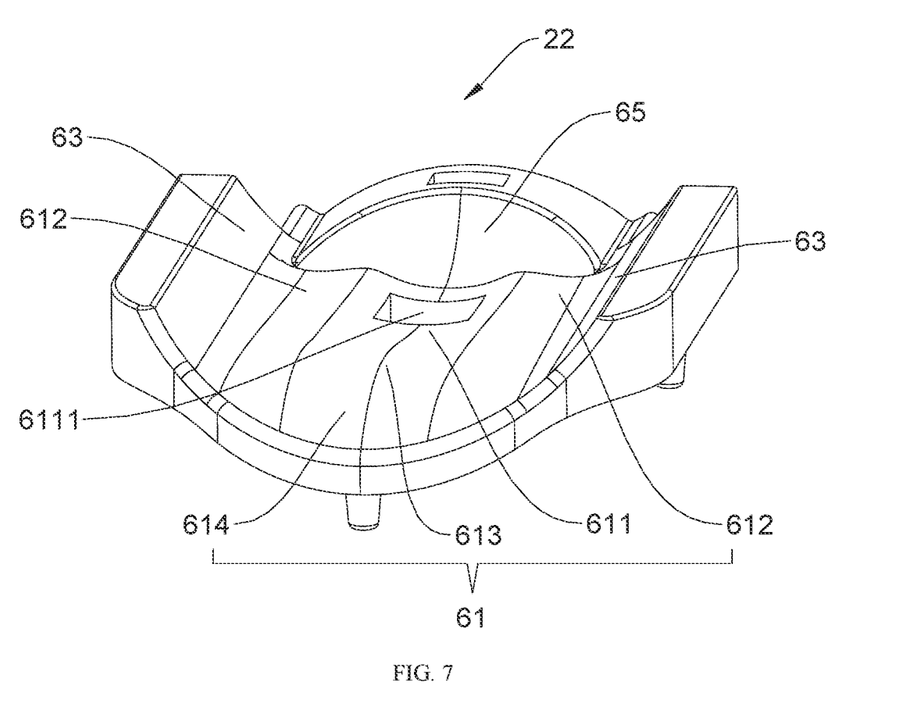
FIG. 7 is a schematic diagram of the structure of the lower finger pad in FIG. 2.

As shown in FIG. 7, the middle area of the arc-shaped first contact surface 61 of the lower finger pad 22 of the present disclosure is also provided with a first concave surface 611 along the transverse direction of the finger. A second concave surface 612 is formed on each of both sides of the first concave surface 611 of the first contact surface 61. The curvature of the first concave surface 611 is greater than the curvature of the second concave surface 612. Both the first concave surface 611 and the second concave surface 612 can be adaptive to the shape of the finger surface such as the pulp of the finger or the dorsal of the finger. In the embodiment of the present disclosure, each side of the two sides of the first concave surface 611 may be provided with one or more second concave surfaces 612. As shown in FIG. 5, the cross-sections of the first concave surface 611 and the second concave surface 612 are inwardly concave arcs. The arc radius of the first concave surface 611 is smaller than the arc radius of the second concave surface 612. The first concave surface 611 is more curved than the second concave surface 612. That is, the arc radius of the first concave surface 611 is smaller to adapt to the thin finger, and the arc radius of the second concave surface 612 is larger to be adaptive to the thick finger.

Alternatively, as shown in FIG. 5, the first concave surface 611 of the present disclosure and the second concave surfaces 612 on both sides of first concave surface 611 are arc-transitioned to form a wavy arc surface. The arc transition is arranged to make the first concave surface 611 and the second concave surface 612 fit the pulp of the finger better. Since the lower finger pad 22 of the present disclosure is provided with the first concave surface 611 and the second concave surfaces 612 in the contact area of the pulp of the finger.

When the finger to be measured is a thin finger, the first concave surface 611 can completely wrap the edges of the pulp of the thin finger, and shield the edges of the pulp of the thin finger, avoiding the interference of light leakage when measuring the thin finger. When the finger to be measured is a thick finger, the first concave surface 611 wraps the middle part of the pulp of the thick finger, and the second concave surfaces 612 wrap the edges of the pulp of the thick finger. The first concave surface 611 and the second concave surfaces 612 are combined to wrap the thick finger, and shield the edges of the thick finger, which also avoids the interference of light leakage when measuring the thick finger. In this way, the finger clip type oximetry device 1 in the embodiment of the present disclosure can be adaptive to the blood oxygen measure of thin finger and the blood oxygen measure of thick fingers, which improves the application range and measurement accuracy of the finger clip type oximetry device 1 of the present disclosure.

Figure 4:
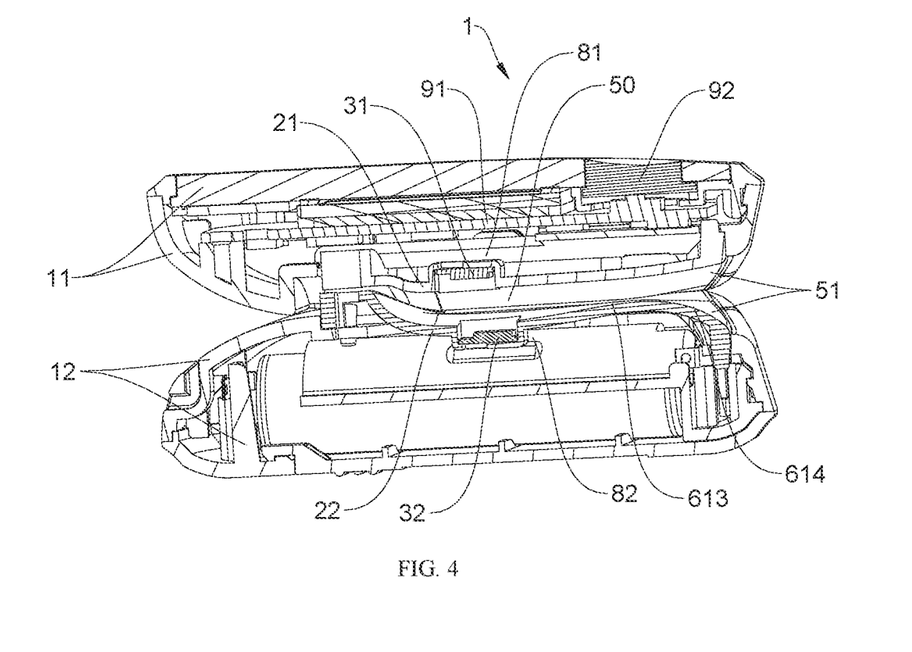
FIG. 4 is a second schematic sectional view of the structure in FIG. 1.
Figure 8:
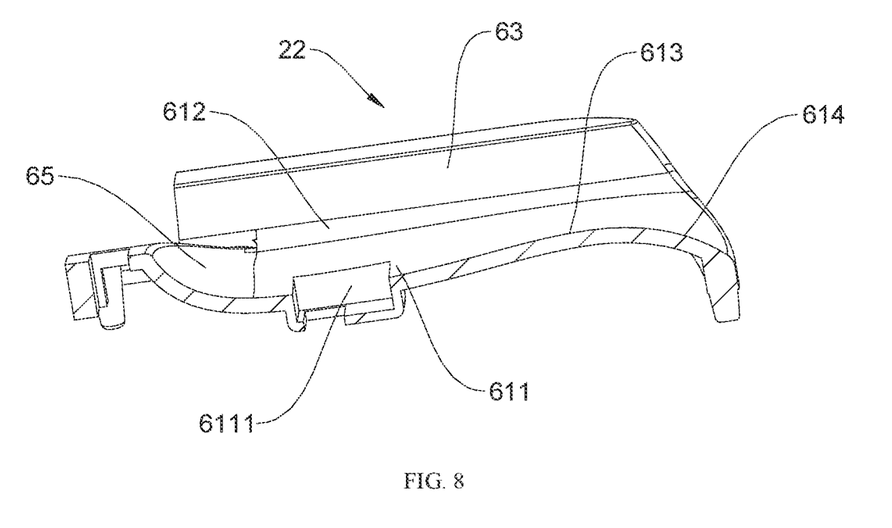
FIG. 8 is a schematic sectional view of the structure of FIG. 7.

Further, as shown in FIG. 6, a third concave surface 622 is arranged along the transverse direction of the finger at the middle area of the second contact surface 62 of the upper finger pad 21 of the present disclosure. Each of both sides of the third concave surface 622 of the second contact surface 62 is provided with a fourth concave surface 623. The curvature of the third concave surface 622 is greater than the curvature of the fourth concave surface 623. In this way, the upper finger pad and the lower finger pad each have two-section concave structure, which can further be adaptive to fingers of different thicknesses for oximetry. As shown in FIGS. 4 and 8, further, the first concave surface 611 of the lower finger pad 22 of the present disclosure extends along the direction of the opening 51 of the accommodating cavity 50, to provide with a first arc surface 613 and a second arc surface 614 sequentially. The first arc surface 613 protrudes upward to gradually reduce the accommodating cavity 50 along the direction of the opening 51, and the second arc surface 614 is sunken downward to enlarge the opening 51.

The upper finger pad and the lower finger pad of the traditional finger clip type oximetry device mainly let a closed elastic force maintain between the upper finger pad and the lower finger pad through a spring structure, so that a wearing friction force is provided when the finger is put on, so as to prevent the finger from slipping off. However, since the fingertip of a human finger is usually thin and the root is thick, the traditional finger clip type oximetry device has poor slip resistance. In the present disclosure, the lower finger pad 22 extends along the direction of the opening 51 of the accommodating cavity 50 to successively provide with the first arc surface 613 and the second arc surface 614 in an "S" shape. The first arc surface 613 protrudes upward to gradually reduce the accommodating cavity 50 along the direction of the opening 51, making the accommodating cavity 50 narrow at the position of the second knuckle of the human finger. Combining with the concave and convex shape of the human joints, the "S"-shaped structure can produce a good anti-slip effect, and make the oximetry device comfortable to wear.

The opening 51 of the accommodating cavity 50 is enlarged by the second arc surface 614 sunken downward at the opening 51 of the accommodating cavity 50 to facilitate the insertion of the finger.

Alternatively, as shown in FIGS. 5 to 7, an edge of each of the two second concave surfaces 612 extends upward to form a first light-shielding surface 63 on the lower finger pad 22 respectively, and each of two edges of the second contact surface 62 extends upward to form a second light-shielding surface 64 on the upper finger pad 21 respectively. The first light-shielding surface 63, the second concave surface 612, and the first concave surface 611 form the lower finger pad 22 into an M-like structure. The second light-shielding surface 64 and the second contact surface 62 form the upper finger pad 21 into an M-like structure, and the first light-shielding surface 63 is bonded to the second light-shielding surface 64. The first light-shielding surface 63 is bonded to the second light-shielding surface 64 to prevent the interference of light leakage from both sides of the finger. The M-like structures of the upper finger pad and lower finger pad help the first light-shielding surface 63 to be bonded to the second light-shielding surface 64. The M-like structures are arranged to make the middle area of the upper finger pad and lower finger pad have enough deformation space after the finger is clamped, so as to fit fingers of different thicknesses.

Furthermore, as shown in FIGS. 7 and 8, the lower finger pad 22 is provided with a third light-shielding surface 65 extending upward from a side of the first concave surface 611 away from the opening 51. The third light-shielding surface 65 can prevent interference of light leakage in front of the fingertip, thereby further avoiding interference of light leakage. Alternatively, the third light-shielding surface 65 is adaptive to the shape of the fingertip, so as to facilitate the placement of the fingertip and improve the wearing comfort.

Continuing to refer to FIG. 5, the first concave surface 611 in the embodiment of the present disclosure is provided with a first mounting port 6111, and the receiver 32 is arranged in the first mounting port 6111. The second contact surface 62 is provided with a second mounting port 621 at a position relative to the first mounting port 6111, and the light emitter 31 is arranged in the second mounting port 621. The mounting positions of the receiver 32 and the light emitter 31 can be interchanged.

Alternatively, the first mounting port 6111 is provided with a concave transparent contact layer 70 adaptive to the shape of the finger surface on the surface of the receiver 32 and the second mounting port 621 is provided with another concave transparent contact layer 70 adaptive to the shape of the finger surface on the surface of the light emitter 31. The transparent contact layer 70 prevents the finger from directly contacting the light emitter 31 and the receiver 32. On the one hand, it can protect the light emitter 31 and the receiver 32. On the other hand, the transparent material is arranged to ensure the normal operation of the light emitter 31 and the receiver 32. At the same time, the concave shape of the transparent contact layer 70 can be adaptive to the shape of the surface of the finger, so that the finger can contact and fit the transparent contact layer 70 well.

As shown in FIGS. 4 and 5, the shell 10 in the embodiment of the present disclosure includes an upper shell 11 and a lower shell 12. The upper finger pad 21 is fixed to the upper shell 11, and the lower finger pad 22 is fixed to the lower shell 12. The rotating mechanism 40 is provided between the upper shell 11 and the lower shell 12. The upper shell 11 and the lower shell 12 of the present disclosure have a supporting function, and at the same time have the function of shielding the upper finger pad 21 and the lower finger pad 22 from external light and preventing the interference of the external light.

Figure 1:
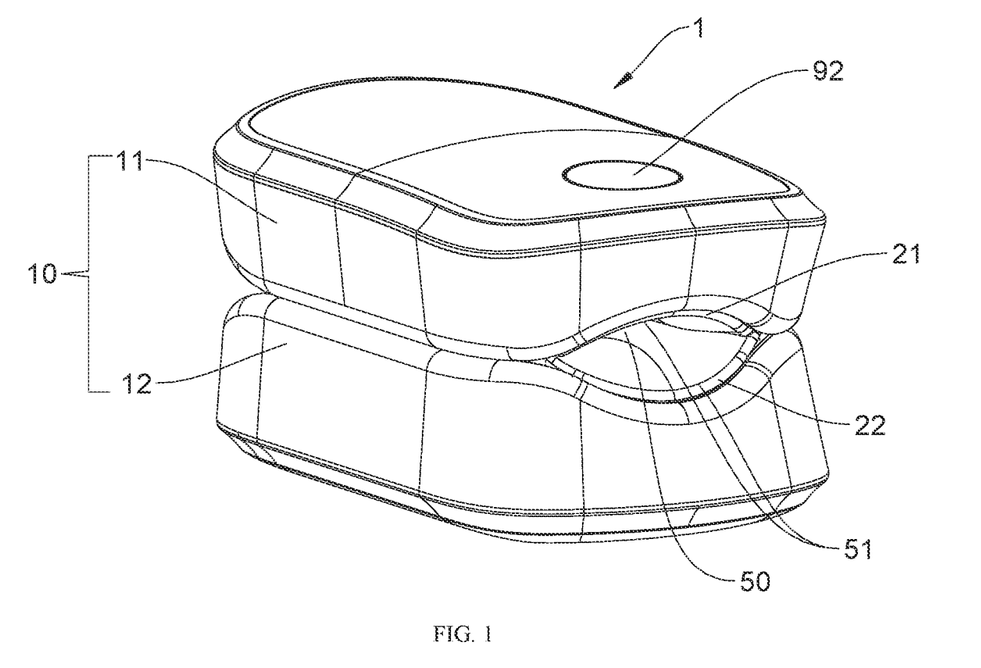
FIG. 1 is a schematic structural diagram of a first embodiment of a finger clip type oximetry device adaptive to thick and thin fingers according to the present disclosure.
Figure 2:
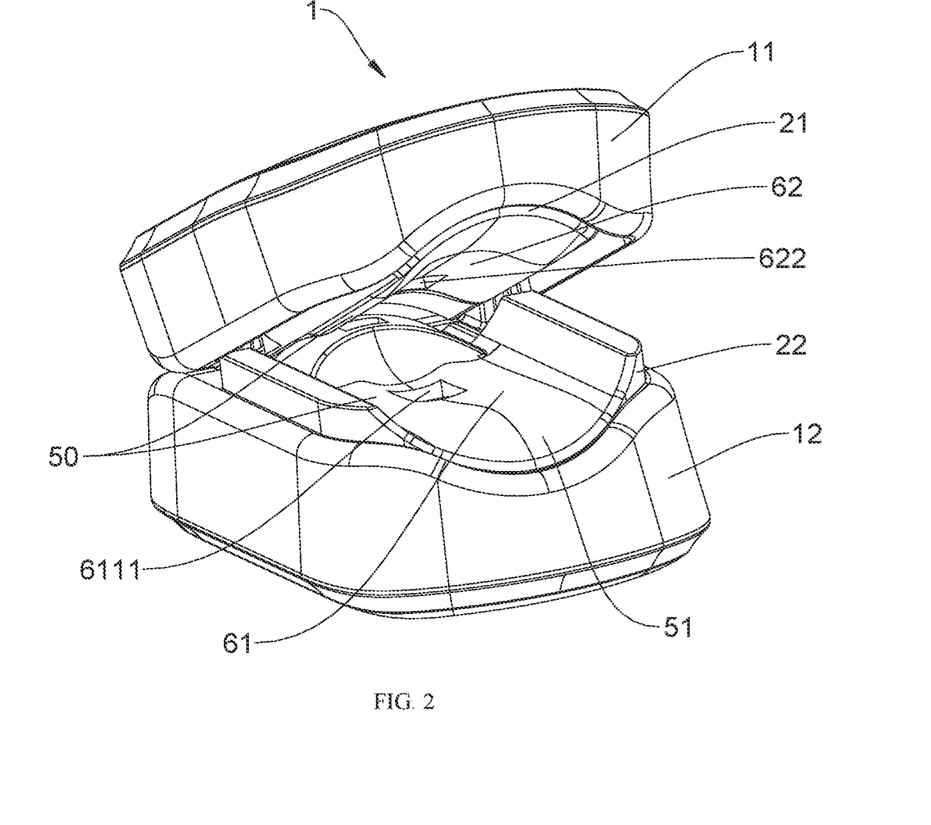
FIG. 2 is a schematic diagram of the structure of FIG. 1 in an open state.
Figure 3:
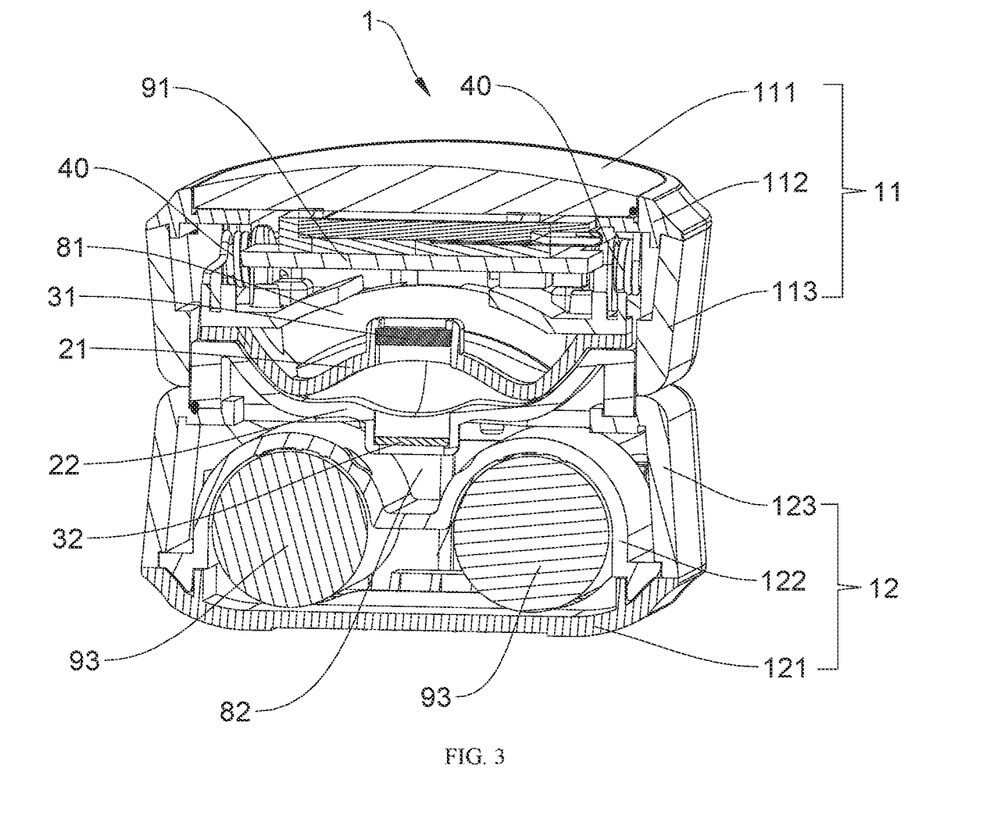
FIG. 3 is a first schematic sectional view of the structure of FIG. 1.
Figure 9:
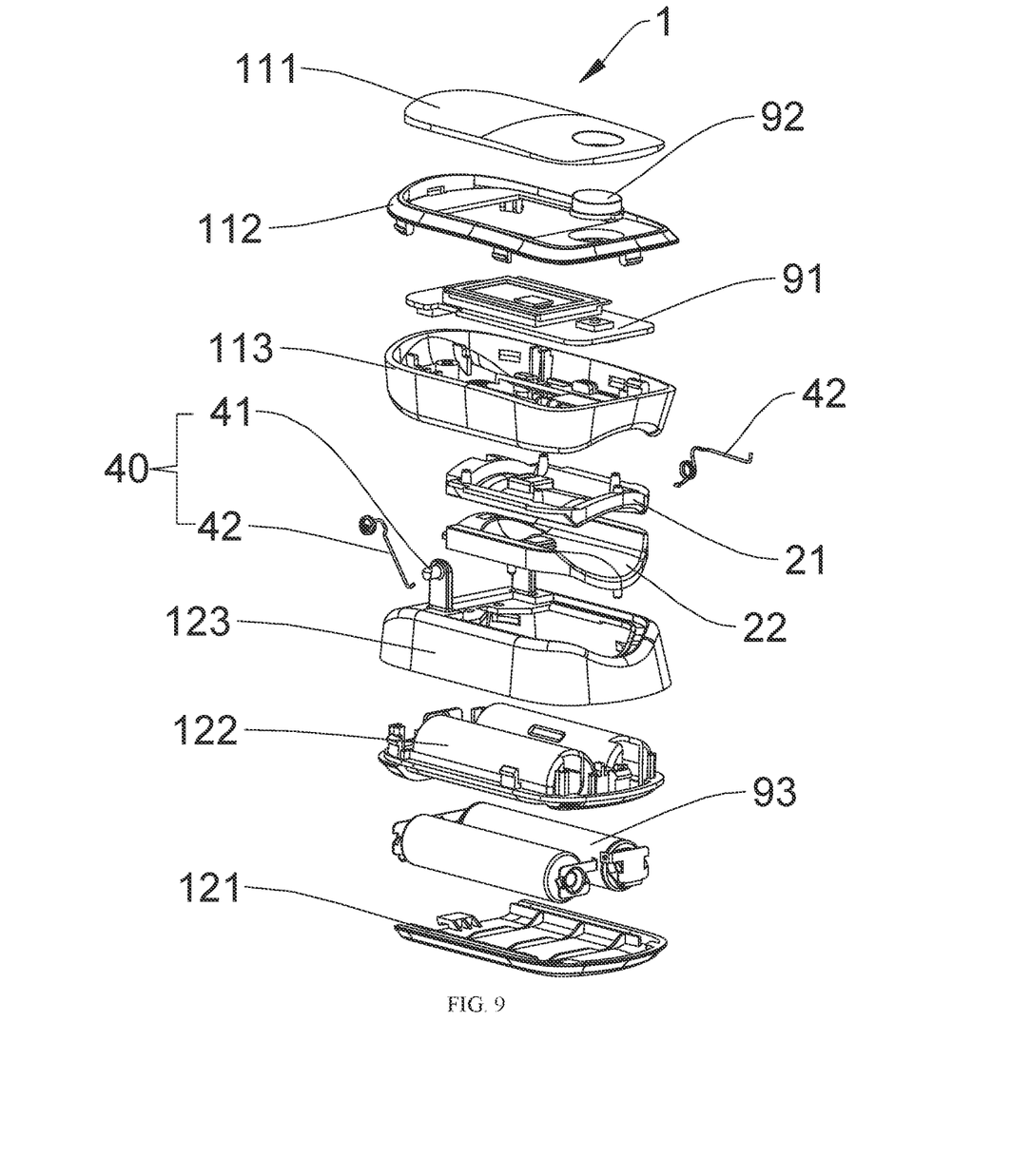
FIG. 9 is an exploded schematic diagram of the structure of FIG. 1.

Specifically, as shown in FIGS. 3 and 9, the upper shell 11 includes an upper cover 111, an upper bracket 112, and a first outer shell 113 that are connected in sequence, and the lower shell 12 includes a lower cover 121, a lower bracket 122, and a second outer shell 123 connected in sequence. The end part 211 of an edge of the M-like structure of the upper finger pad 21 is fixed to the first outer shell 113, and the end part 211 of an edge of the M-like structure of the lower finger pad 22 is fixed to the second outer shell 123. The rotating mechanism 40 is provided between the first outer shell 113 and the second outer shell 123. A first cavity 81 is provided between the side of the upper finger pad 21 facing away from the accommodating cavity 50 and the upper bracket 112, and a second cavity 82 is provided between the side of the lower finger pad 22 facing away from the accommodating cavity 50 and the lower bracket 122. The first cavity 81 and the second cavity 82 are arranged to fully be adaptive to the deformation of the upper finger pad 21 and the lower finger pad 22 after the finger is put in, and prevent the shell 10 from interfering with the upper finger pad and the lower finger pad and affecting the entering of the finger. The fixing positions of the upper finger pad 21 and the lower finger pad 22 to the shell 10 are respectively the end part 211 of the edge of the M-like structure of the upper finger pad 21 and the end 221 of the edge of the M-like structure of the lower finger pad 22, so that there is an space between the middle part of the M-like structure of the upper finger pad 21 and the housing 10, and there is another space between the middle part of the M-like structure of the lower finger pad 22 and the housing 10, to provide deformation spaces as much as possible, thereby making full use of the deformation spaces of the M-like structures of the upper finger pad 21 and the M-like structure of the lower finger pad 22.

Figure 10:
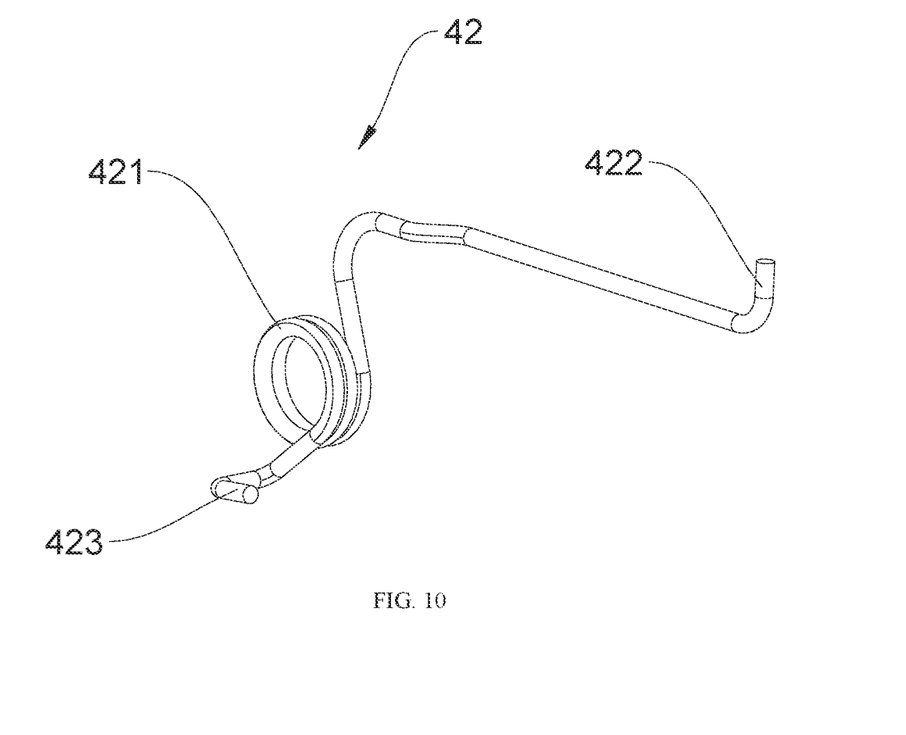
FIG. 10 is a schematic diagram of a structure of a spring in FIG. 9.

As an embodiment, the rotating mechanism 40 of the present disclosure includes a mounting post 41 and a spring 42. The mounting post 41 is arranged on the first outer shell 113 or the second outer shell 123. The middle part 421 of the spring 42 is fixed to the mounting post 41. A first end 422 of the spring 42 abuts against the first outer shell 113, and a second end 423 of the spring 42 abuts against the second outer shell 123. As shown in FIG. 10, the mounting post 41 of the present disclosure is arranged on the second outer shell 123, and the spring 42 provides resilience after the first outer shell 113 and the second outer shell 123 are opened. Alternatively, a control circuit board 91 is further provided between the upper bracket 112 and the first housing 113 in the embodiment of the present disclosure. The control circuit board 91 is connected to a switch 92 exposed on the upper cover 111. The lower bracket 122 is further provided with a battery mounting portion 1221, and the battery mounting portion 1221 is provided with a battery 93. The control circuit board 91 has a data processing function, and can independently complete the test without external equipment, directly making the finger clip type oximetry device 1 of the present disclosure into a separate oximetry instrument. The switch 92 is opened and closed to control the operation of the circuit board 91, and the battery 93 enables the finger clip type oximetry device 1 in the embodiment of the present disclosure to work normally without being connected to an external power source.

It can be understood that the finger clip type oximetry device 1 of the embodiment of the present disclosure may also have a display screen exposed on the upper cover 111. The display screen and the control circuit board 91 are in communication connection, so that the display screen is convenient for the user to directly watch the measurement result.

In the finger clip type oximetry device 1 adaptive to thick and thin fingers proposed in the embodiment of the present disclosure, the first concave surface 611 and the second concave surfaces 612 are provided on the first contact surface 61 with the contact area where one of the upper finger pad 21 and the lower finger pad 22 contact the pulp of the finger. The first concave surface 611 is arranged in the middle area of the first contact surface 61 along the transverse direction of the finger, and the second concave surface 612 is arranged on each of both sides of the first concave surface 611. The curvature of the first concave surface 611 is greater than the curvature of the second concave surface 612. The first concave surface 611 and the second concave surface 612 are adaptive to the shape of the finger surface. The finger clip type oximetry device 1 in the embodiment of the present disclosure can be adaptive to the thin finger and the thick finger, avoiding interference of light leakage when measuring fingers of different thicknesses and affecting the measurement results, and improving the scope of application of the product when measuring.

It should be noted that the embodiments of the device described above are only illustrative, and the units described as separate components may or may not be physically separated, and the components displayed as units may or may not be physically separate. A component displayed as a unit may or may not be a physical unit, that is, it may be located in one place, or may be distributed to multiple network units. Some or all of the modules can be selected according to actual needs to achieve the objectives of the solutions of the embodiments. In addition, in the drawings of the device embodiments provided by the present disclosure. The connection relationship between the modules indicates that there is a communication connection between them, which can be specifically implemented as one or more communication buses or signal lines. Those of ordinary skill in the art can understand and implement without creative work.

Described above are only the exemplary embodiments of the present disclosure, and do not limit the scope of the present disclosure. Under the inventive concept of the present disclosure, any equivalent structural transformations made using the contents of the description and drawings of the present disclosure, or direct/indirect application in other related technical fields are included in the scope of patent protection of the present disclosure.

What is claimed is:

1. A finger clip type oximetry device adaptive to thick and thin fingers, comprising:
    a shell, wherein the shell comprises an upper shell and a lower shell;
    an upper finger pad, a lower finger pad, a light emitter, and a receiver provided in the shell, wherein an accommodating cavity is enclosed by a wall surface of the upper finger pad and a wall surface of the lower finger pad for placing a finger to be measured, and the upper finger pad is fixed to the upper shell, and the lower finger pad is fixed to the lower shell; and
    a rotating mechanism for relatively opening or clamping the upper finger pad and the lower finger pad, wherein the rotating mechanism is arranged between the upper shell and the lower shell, the rotating mechanism is an elastic clamping mechanism or a clamping mechanism capable of opening or clamping and comprises a mounting post and a spring;
    wherein one end of the accommodating cavity is provided with an opening, wherein an arc-shaped first contact surface is provided at a contact area where the lower finger pad contacts a pulp of the finger in the accommodating cavity, and an arc-shaped second contact surface is provided at a contact area where the upper finger pad contacts a dorsal of the finger in the accommodating cavity, and
    wherein a first concave surface is arranged on a middle area of the arc-shaped first contact surface along a transverse direction of the finger, each of both sides of the first concave surface of the first contact surface is formed with a second concave surface, and a curvature of the first concave surface is greater than a curvature of the second concave surface;
    wherein the first concave surface and the second concave surface are adaptive to the shape of the finger, the first concave surface and the second concave surfaces on both sides of first concave surface are arc-transitioned to form a wavy arc surface;
    wherein the lower finger pad is provided with a first light-shielding surface extending upward on an edge of each of the two second concave surfaces, wherein the upper finger pad is provided with a second light-shielding surface extending upward on each of two edges of the second contact surface, wherein the first light-shielding surface, the second concave surface and the first concave surface form the lower finger pad into an M-like structure, wherein the second light-shielding surface and the second contact surface form the upper finger pad into another M-like structure, and wherein the first light-shielding surface is attached to the second light-shielding surface when the upper finger pad and the lower finger pad are clamped by the rotating mechanism;
    wherein a first cavity is provided between a side of the upper finger pad facing away from the accommodating cavity and an upper bracket.

2. The finger clip type oximetry device adaptive to thick and thin fingers of claim 1, wherein the first concave surface of the lower finger pad extends along a direction of an opening of the accommodating cavity to provide with a first arc surface and a second arc surface sequentially, and wherein the first arc surface protrudes upward to gradually reduce the accommodating cavity along the direction of the opening, and the second arc surface is sunken downward to enlarge the opening.

3. The finger clip type oximetry device adaptive to thick and thin fingers of claim 2, the first arc surface and the second arc surface form an "S" shape.

4. The finger clip type oximetry device adaptive to thick and thin fingers of claim 1, wherein the lower finger pad is provided with a third light-shielding surface extending upward from a side of the first concave surface away from the opening.

5. The finger clip type oximetry device adaptive to thick and thin fingers of claim 1, wherein the first concave surface is provided with a first mounting port, and a receiver is mounted in the first mounting port,
   wherein the second contact surface is provided with a second mounting port at a position relative to the first mounting port, and a light emitter is mounted in the second mounting port, and
   wherein a mounting position of the receiver and a mounting position of the light emitter are interchangeable.

6. The finger clip type oximetry device adaptive to thick and thin fingers of claim 5, wherein a surface of the receiver on the first mounting port and a surface of the light emitter on the second mounting port are respectively provided with a concave transparent contact layer adaptive to a shape of a surface of the finger.

7. The finger clip type oximetry device adaptive to thick and thin fingers of claim 1, wherein the upper shell comprises an upper cover, the upper bracket, and a first outer shell connected in sequence, and the lower shell comprises a lower cover, a lower bracket, and a second outer shell connected in sequence,
   wherein an end of an edge of the M-like structure of the upper finger pad is fixed to the first outer shell, and an end of an edge of the M-like structure of the lower finger pad is fixed to the second outer shell,
   wherein the rotating mechanism is arranged between the first outer shell and the second outer shell, and
   wherein the first cavity is arranged between the side of the upper finger pad facing away from the accommodating cavity and the upper bracket; and a second cavity is arranged between a side of the lower finger pad facing away from the accommodating cavity and the lower bracket.

8. The finger clip type oximetry device adaptive to thick and thin fingers of claim 7, wherein the rotating mechanism comprises a mounting post arranged on the first outer shell or the second outer shell and a spring, wherein a middle of the spring is fixed to the mounting post, a first end of the spring abuts against the first outer shell, and a second end of the spring abuts against the second outer shell.

9. The finger clip type oximetry device adaptive to thick and thin fingers of claim 8, wherein a control circuit board is provided between the upper bracket and the first outer shell, and connected to a switch exposed on the upper cover, and wherein the lower bracket is provided with a battery mounting portion where a battery is mounted.

10. The finger clip type oximetry device adaptive to thick and thin fingers of claim 9, the control circuit board is connected to a switch exposed on the upper cover.

11. The finger clip type oximetry device adaptive to thick and thin fingers of claim 9, further comprising:
    a display screen exposed on the upper cover, and in communication connection with the control circuit board.

12. The finger clip type oximetry device adaptive to thick and thin fingers of claim 1, wherein a third concave surface is arranged along the transverse direction of the finger at a middle area of the second contact surface,
    wherein each of both sides of the third concave surface of the second contact surface is formed with a fourth concave surface, and
    wherein a curvature of the third concave surface is greater than a curvature of the fourth concave surface.

13. The finger clip type oximetry device adaptive to thick and thin fingers of claim 1, wherein the light emitter and the receiver are connected to an external measurement system through a cable.

14. The finger clip type oximetry device adaptive to thick and thin fingers of claim 1, wherein the upper finger pad and the lower finger pad are made of flexible materials.

15. The finger clip type oximetry device adaptive to thick and thin fingers of claim 1, wherein the shell is an integral structure or a structure with an upper shell and a lower shell.

* * * * *